(12) United States Patent
Zaykova-Feldman et al.

(10) Patent No.: US 7,755,372 B2
(45) Date of Patent: Jul. 13, 2010

(54) METHOD FOR AUTOMATED STRESS TESTING OF FLIP-CHIP PACKAGES

(75) Inventors: Lyudmila Zaykova-Feldman, Dallas, TX (US); Thomas M. Moore, Dallas, TX (US)

(73) Assignee: Omniprobe, Inc., Dallas, TX (US)

( * ) Notice: Subject to any disclaimer, the term of this patent is extended or adjusted under 35 U.S.C. 154(b) by 140 days.

(21) Appl. No.: 12/238,906

(22) Filed: Sep. 26, 2008

(65) Prior Publication Data

US 2009/0015274 A1 Jan. 15, 2009

Related U.S. Application Data

(62) Division of application No. 11/367,562, filed on Mar. 3, 2006, now Pat. No. 7,446,542.

(60) Provisional application No. 60/658,913, filed on Mar. 4, 2005.

(51) Int. Cl.
*G01R 31/302* (2006.01)

(52) U.S. Cl. ..................................... 324/750

(58) Field of Classification Search ......... 324/750–752, 324/760, 765, 158.1; 73/12.01–12.14, 587, 73/750; 702/193, 141, 190, 174, 184
See application file for complete search history.

(56) References Cited

U.S. PATENT DOCUMENTS 5,319,977 A * 6/1994 Quate et al. .................. 73/606
6,877,365 B2 * 4/2005 Watanabe et al. ............. 73/105

\* cited by examiner

*Primary Examiner*—Ha Tran T Nguyen
*Assistant Examiner*—Tung X Nguyen
(74) *Attorney, Agent, or Firm*—John A. Thomas

(57) ABSTRACT

Methods for testing flip-chip packages includes aligning a microscope and a test engine. The package under test is placed between the microscope and the test engine, and an acoustic transducer is attached to the package under test. The test engine delivers an impact to the package under test on the side of the package opposite its ball-grid array. Acoustic information and image information from the package under test is recorded. In alternate embodiments, a sequence of packages may be automatically tested.

10 Claims, 9 Drawing Sheets

METHOD FOR AUTOMATED STRESS TESTING OF FLIP-CHIP PACKAGES

CLAIM FOR PRIORITY

This application is a divisional application of U.S. patent application Ser. No. 11/367,562, filed Mar. 3, 2006 Now U.S. Pat. No. 7,446,542, which in turn claims the priority of U.S. Provisional Patent Application Ser. No. 60/658,913, filed Mar. 4, 2005, both of which applications are incorporated into the present application by reference.

BACKGROUND

1. Technical Field

This application is directed to a method of testing flip-chip packages for integrated circuits.

2. Background Art

Flip-chip technology is defined as mounting the chip on a substrate using a variety of interconnect materials and methods as long as the chip surface, i.e. the active circuit, is facing the substrate. In this technique, solder bumps are attached to the input-output pads of the die at the wafer level. The flip-chip technique is the high-performance alternative to wire bonding techniques. Flip chips are cost effective and allow the realization of very slim and compact products, with increased I/O density and system miniaturization.

The most well-known and successful flip-chip technology today, IBM's solder-bumped flip-chip technology, evolved into the ball-grid array (BGA) packaging of integrated circuits. BGA packaging is scaling into smaller solder ball pitches and smaller individual solder ball sizes. Due to this smaller size, the requirements on packaging reliability, including the solder joint reliability, are becoming stricter. There are several different testing techniques of solder joint reliability in use in the industry, concentrating mostly on thermal performance.

There is a need for a mechanical stress testing technique, preferably using a relatively simple and inexpensive instrument. The ideal test environment would be the one very close to the application environment, with the possibility to produce an impact on the flip-chip package in a controllable way. The proposed method and apparatus of flip-chip test environment describes a testing process including different types of impact vehicles.

DESCRIPTION

Figure 1:
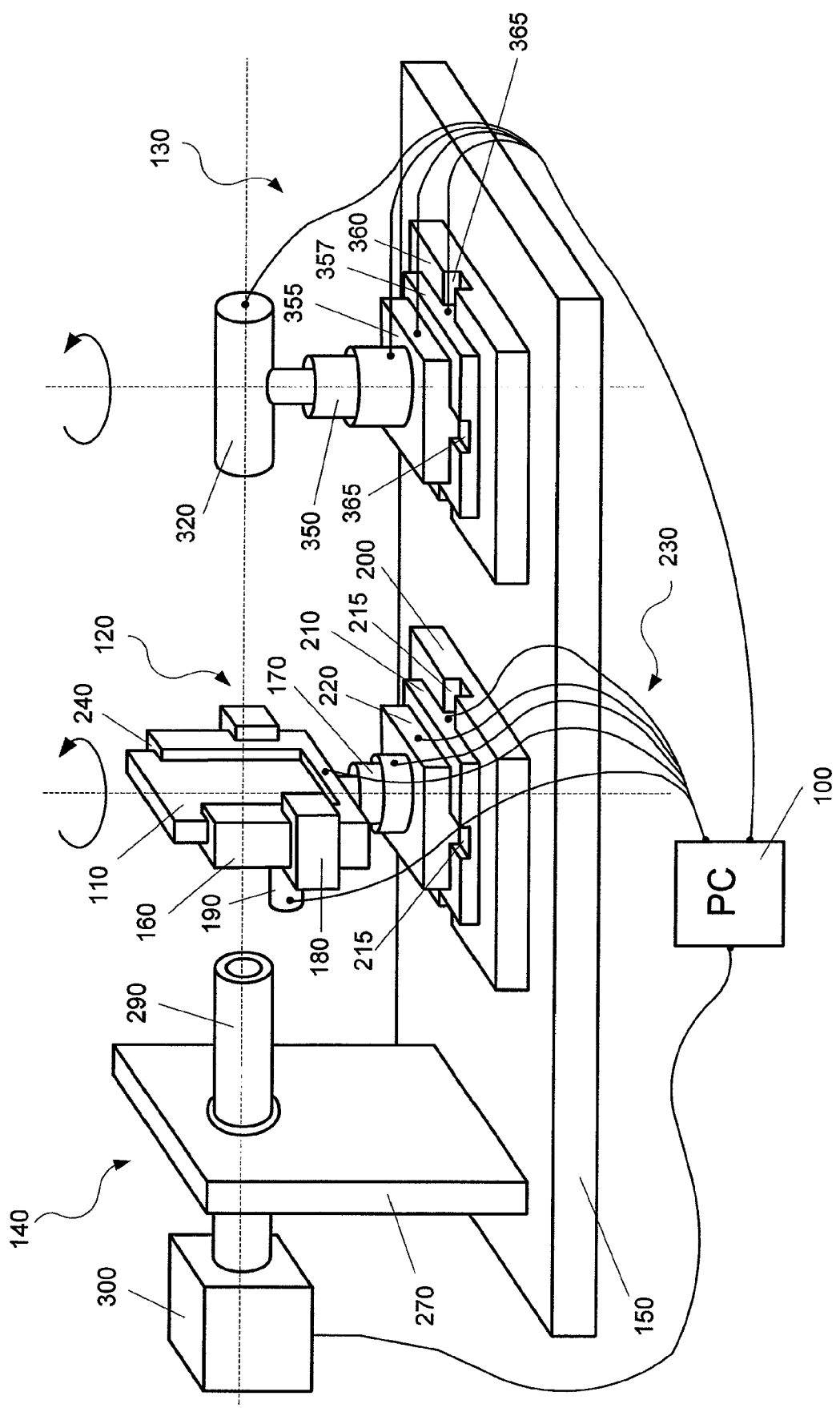
FIG. 1 is a perspective view of a mechanical stress testing system.

The preferred embodiment includes a novel method and apparatus for mechanical flip-chip die and BGA package testing environment. In the preferred embodiment, the testing system comprises three major components: the sample stage, the test engine stage and the monitoring stage. The apparatus may also include a computer for process control and an optional pick-and-place robot for placement of sample packages.

The Sample Stage

In the preferred embodiment, a sample stage (120) comprises a base (160) where the sample package (110) is inserted, a telescopic stand (170) holding the base (160), the frame (180) holding the acoustic transducer (190), and two small platforms (200, 210) for horizontal movement in two perpendicular directions.

The lower small platform (200) is rigidly attached to a base platform (150), where all three stages are located. Both lower (200) and middle (210) small platforms comprise two tracks (215) intended for the movement of each small platform in one of the perpendicular horizontal directions.

The base (160) holding the package (110) is set on a telescopic stand (170). The telescopic stand (170) is rigidly attached to an upper small platform (220). The telescopic stand (170) allows for vertical movement of the base (160) and rotation of the base (160) around its axis, which coincides with that of the telescopic stand (170).

The outer frame (180) holds an acoustic transducer (190) attached to the package base (160). The outer frame (180) can change its position relative to the base (160). The acoustic transducer (190) is mounted in an opening in the frame (180). The inner end of the acoustic transducer (190) is directly connected to a package (110), and an acoustic gel is applied where the contact between the package (110) and the acoustic transducer (190) is made to ensure good acoustic contact. Suitable acoustic transducers are manufactured by Panametrics, Inc. The position of the frame (180) holding the acoustic transducer (190) can be manually or automatically adjusted to make contact between the sample package (110) and the acoustic transducer (190) in a location that will assure the best performance of the acoustic transducer (190).

As shown in FIG. 1, the small platforms (200, 210, 220), the telescopic stand (170) and the acoustic transducer (190) are connected by appropriate electrical wiring (230) to a controlling computer (100) to ensure their proper movement and the feedback control. These wires (230) can be extended either outside or inside the stage (120). Motion control and feedback control can be accomplished by means known in the art, using actuators, position encoders and controlling software such as LabVIEW supplied by National Instruments, Inc., of Austin, Tex.

The base (160) holding the package (110) has vertical rails (240) where the package (110) is inserted and is held for the test. These vertical rails (240) have several clamps (not shown) located at an appropriate distance for each package size. It is possible to insert several packages (110) vertically and conduct the stress test for several packages (110) in one testing session. The packages (110) can be brought to a testing site in a standard JEDEC tray and can be picked up and inserted into the base (160) manually. Alternatively, a conventional autoloader can be used to insert the special JEDEC standard tray into a holder.

The Monitoring Stage

The monitoring stage (260) comprises a stand (270) with an opening (280) for holding an optical microscope (290). A digital camera (300) attached to the optical microscope (290). The optical microscope (290) is used for alignment of the test engine (320) axis and the target area on the package (110), and for the detailed monitoring of the solder ball (330) displacement. The digital camera (300) records the stress test procedure and details of the solder ball (330) displacement. The digital camera (300) operation and the optical microscope (290) focus adjustment are electronically controlled by computer (100) using the motion-control devices mentioned above. All the details of the mechanical stress test procedure shown by the digital camera (300) can be displayed on a computer monitor screen. Only one of the digital camera (300) or optical microscope (290) need be moved.

The Test Engine Stage

The test engine stage (340) comprises the telescopic stand (350) holding the mounting for a test engine (340) and three small platforms (355, 357 and 360) for horizontal movement in two perpendicular directions. The lower small platform (360) is rigidly attached to a base platform (150), where all three major stages are located. The lower (360) and the middle (357) small platforms include two tracks (365) each for the movement in one of the perpendicular horizontal directions. The engine (320) for the mechanical stress testing of a package (110) can be mounted on a telescopic stand (350) on the upper small platform (355), and as discussed below. The mounting of a test engine (320) on a telescopic stand (350) gives the testing system the possibility of easy and fast test engine (320) replacement. The test engine (320) can be any of several alternative devices as described in the following.

The Mechanical Stress Testing Method

Figure 2:
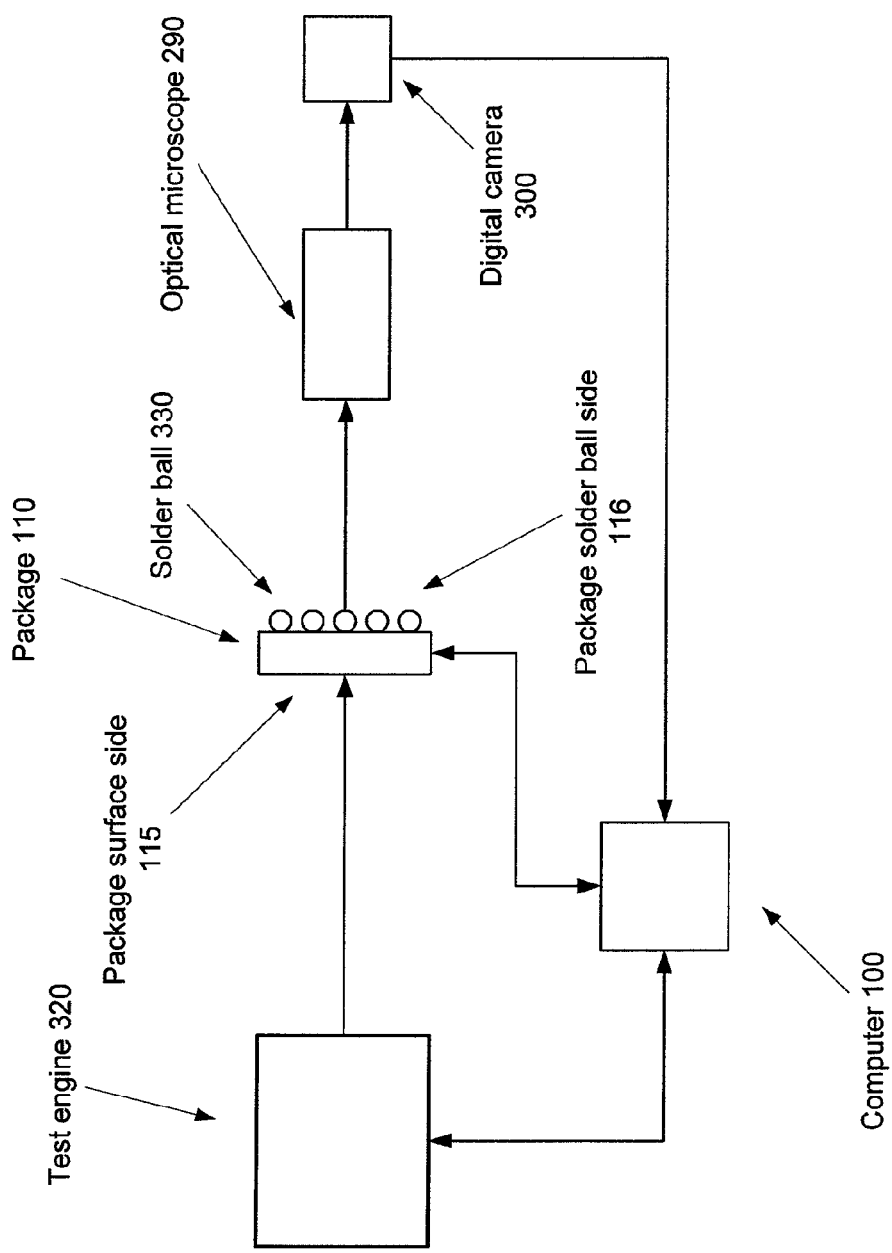
FIG. 2 is a schematic diagram of a mechanical stress testing system.
Figure 3:
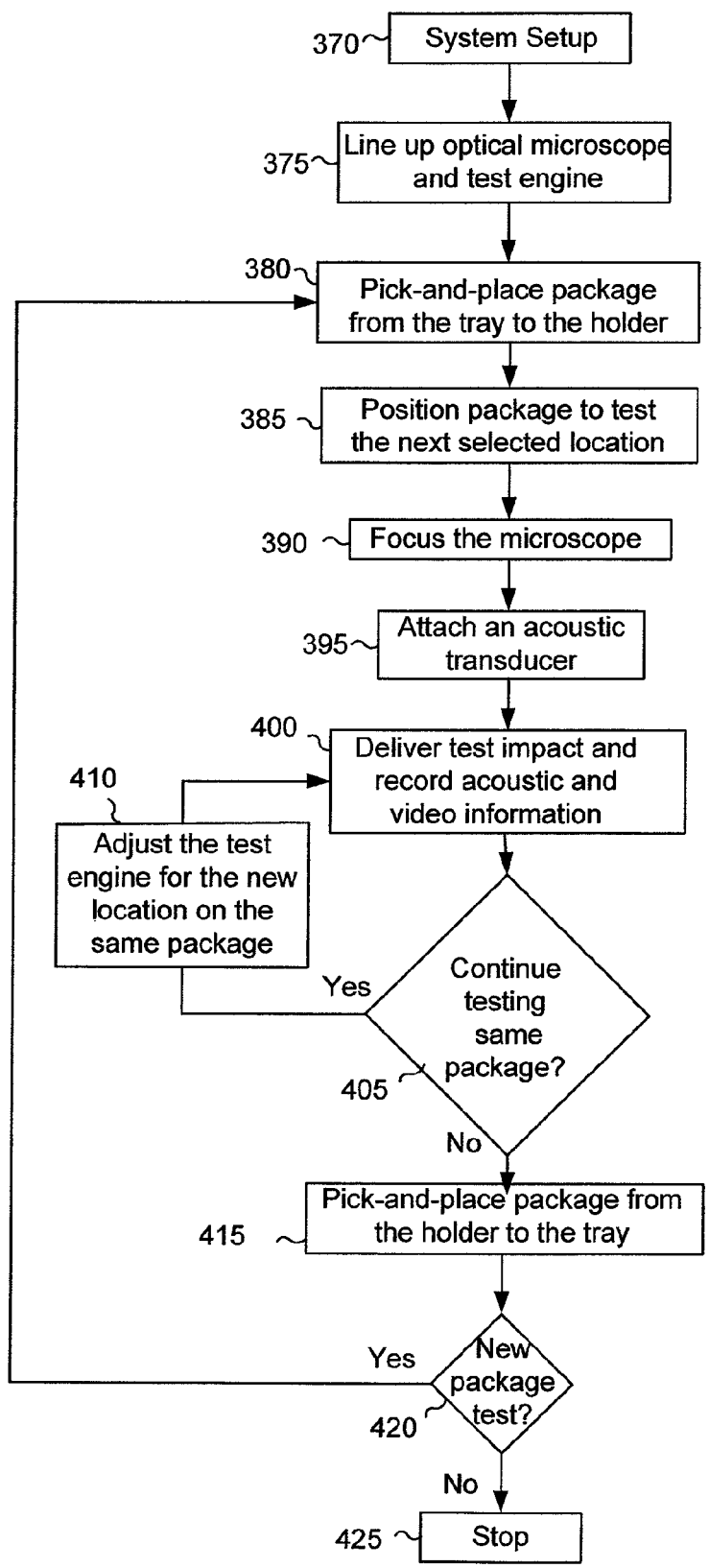
FIG. 3 is a flowchart of a mechanical automated stress testing process.
Figure 4:
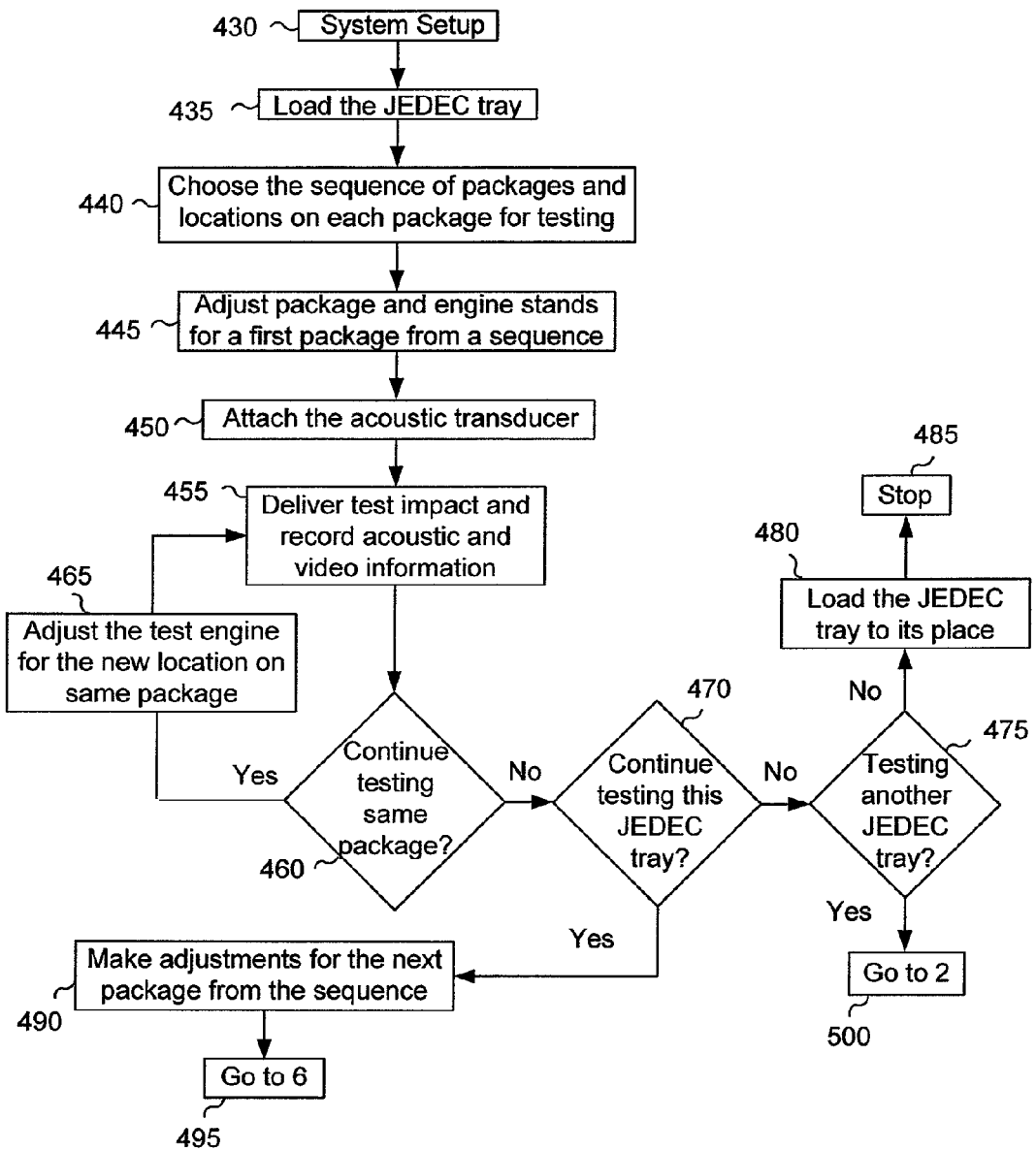
FIG. 4 is a flowchart of an alternative mechanical automated stress testing process.
Figure 5:
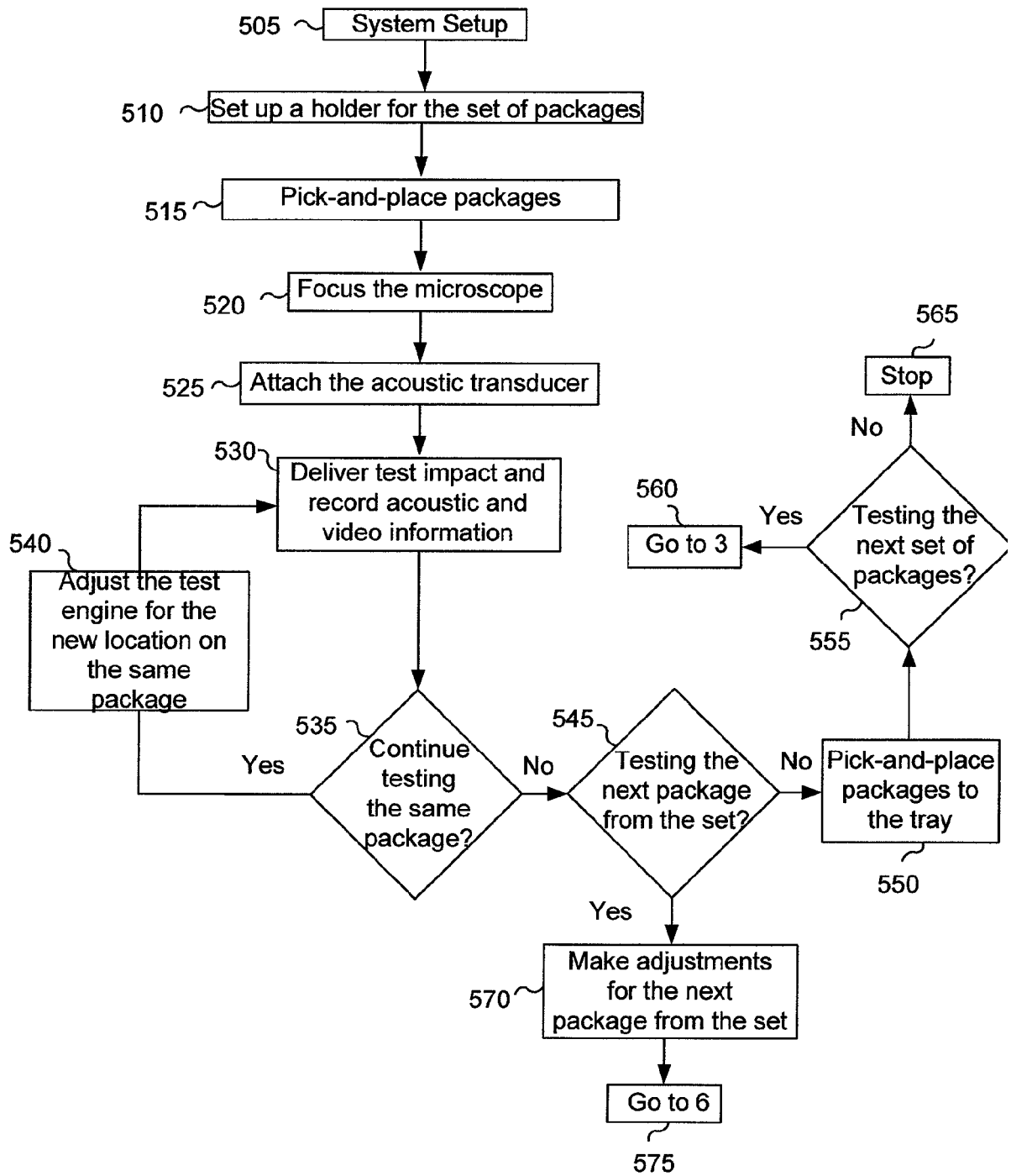
FIG. 5 is a flowchart of an alternative mechanical automated stress testing process.

The package (110) can be mechanically stress tested using the scheme shown in FIG. 2 and the flowcharts shown in FIGS. 3-5. Every package (110) can be picked from the special package tray and placed into the base (160) either manually or using a pick-and-place robot. Alternatively, a JEDEC standard tray can be used. The stress test engine (320) can be chosen from the set described in "The Test Engine Stage" section of this application. Before placing the package (110) in the base (160), the stress test engine (320) axis can be aligned with the optical microscope (290).

One or more packages (110) can be placed in the base (160) in a fixed position. The packages (110) are positioned in a holder base (160) so that the substrate side (115) faces the optical microscope (290). The optical microscope (290) is focused on a solder ball side (116) of the sample package (110). The multi-platform design of the stress test engine (320) and the sample stage setting (120) allows the fine adjustment of the test engine (320) and the package (110) positions.

The package (110) receives an impact from the test engine (320) on the side opposite the side with the solder balls, possibly followed by the displacement of the solder ball (330) directly opposite the point of impact. The solder ball can be even separated from the package, depending on the intensity of the strike and the mechanical strength of the solder ball attachment. This event can be watched on a computer (100) monitor screen and recorded using the optical microscope (290) and the digital camera (300). This method allows the real-time operation and the adjustment of the impact strength to reach the desired result, from a small solder ball (330) displacement up to a crack in the package (110) substrate. The quantitative impact monitoring is being provided by the acoustic transducer (190) attached to a package (110) preferably on the solder ball side (380), but alternatively on the opposite side, on which the test impact is delivered. The accurate measurement of the velocity can be performed using two optical detectors (not shown) in the projectile path. The velocity and the known mass of the projectile can be used to quantify the test procedure.

The mechanical shockwaves originated because of the impact can be transformed into an electric current using the acoustic transducer (190), with its output signal sent to a computer (100). The calibration of the test impact can be performed by detection of the magnitude of the acoustic signal or the characteristic acoustic signature of the impact event using a suitable signal-processing computer program. If using a pick-and-place robot, the entire process can be automated. The automated process flowcharts are shown in FIGS. 3-5. The case of one package is (110) shown in FIG. 3. In this method, it is possible to test as many locations on the surface of a package (110) as needed. The case of testing a set of packages (110) is shown in FIG. 4. During the course of this procedure, the next package (110) is moved to a preferred testing position and tested, until the testing session is finished. Then the robot or an operator can replace the package (110) or a set of packages (110), and the process can be started over again. The case of a JEDEC tray testing is shown in FIG. 5.

In the preferred embodiment, a test engine (320) comprising a pneumatic projectile device is used. A test engine (320) with such a projectile launcher allows impacting any desired location on a package (110) by adjusting its position using the telescopic stand and the movement of the small platforms. The projectiles for this pneumatic device can be solid, or liquid droplets, or of any other appropriate material. The projectiles should be of a known mass and a uniform shape for quantitative and repeatable testing.

Figure 6:
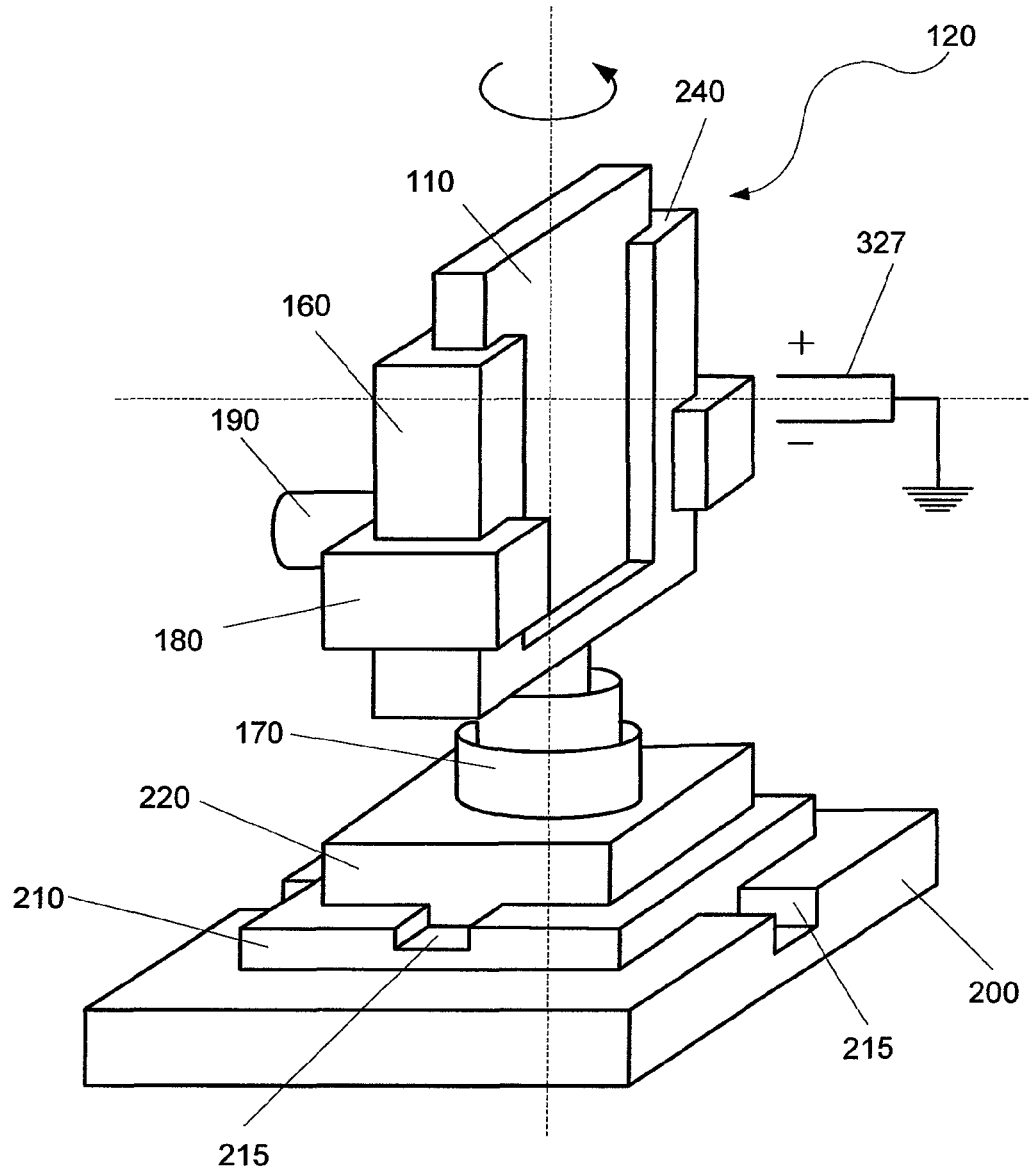
FIGS. 6-9 show alternate embodiments of the test engine.

In alternative embodiment, shown in FIG. 6, an electrical discharge source (327) can be used for flip-chip device stress testing. Such a capacitive discharge device, for example, can deliver an electric pulse to a target position on the device surface and generate the desired shock wave for testing.

Figure 7:
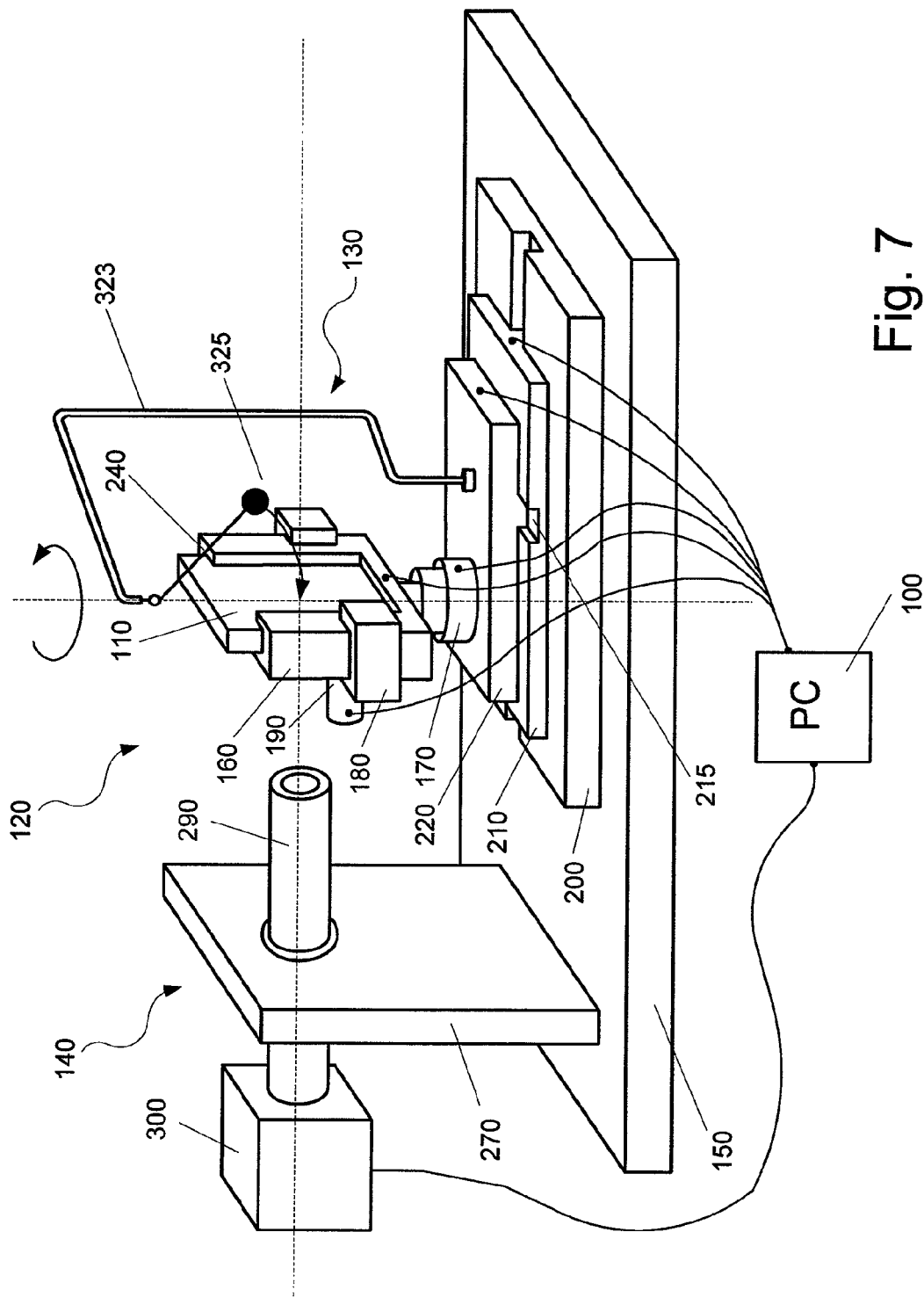

In another alternative embodiment shown in FIG. 7, a small pendulum (325) of known mass and released from a fixed height can be used for testing. The pendulum holder (323) can be positioned at an appropriate distance from the surface of the package (110), which is opposite the solder balls. The impact strength can be determined from the mass of the pendulum (325), the length of the pendulum arm and the release height. The position of an impact on a package surface can be adjusted via changing the position of the package (110).

Figure 8:
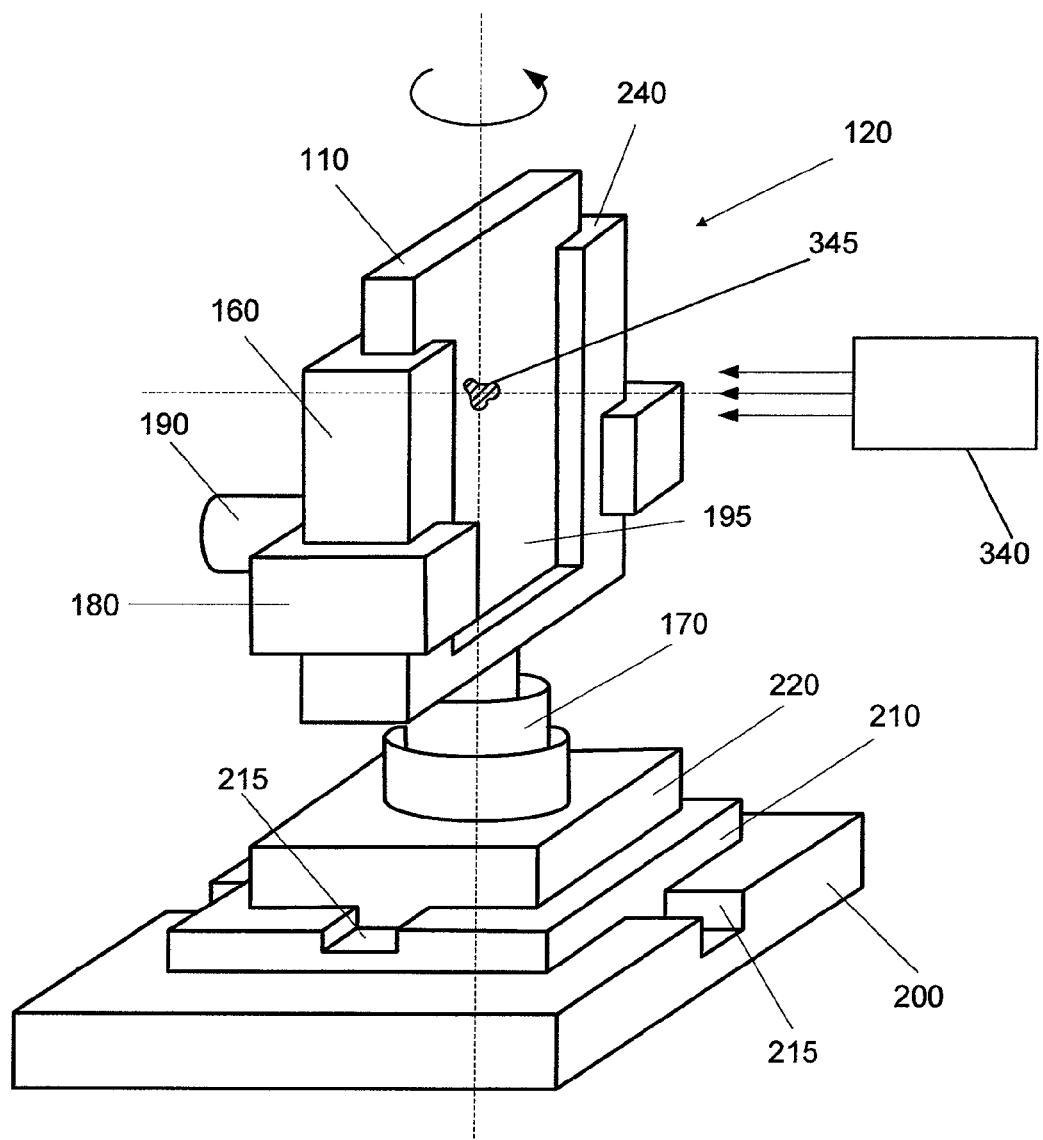

In another alternative embodiment shown in FIG. 8, small chemical or pyrotechnic explosives (345) with predetermined strength can be applied to a flip-chip package surface. For example, tiny drops of explosive material (345) can be deposited and dried at appropriate locations on the surface of the package (110), opposite the solder balls (330). Each of these dried droplets can then be detonated by an energy source (not shown) made part of the test engine (340), such as a laser beam, electric shock or localized heat source.

Figure 9:
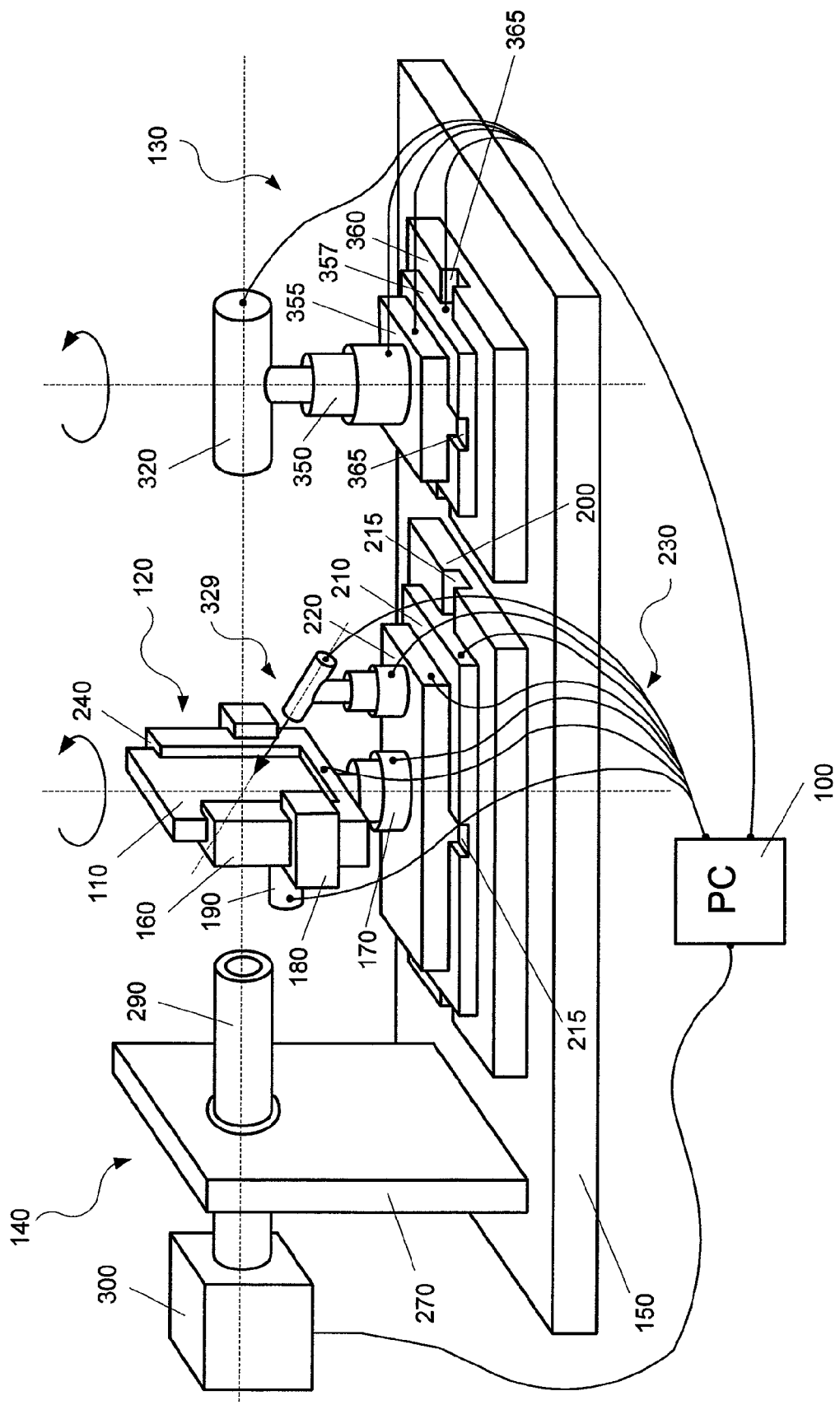

In another alternative embodiment shown in FIG. 9, a microwave radiation source (329) can be applied to either surface of the package (110) to produce a rapid thermal expansion within the package (110). Then a mechanical shockwave is applied as previously discussed to test the solder ball attachment under conditions of elevated temperature.

Since those skilled in the art can modify the specific embodiments described above, we intend that the claims be interpreted to cover such modifications and equivalents.

We claim:

1. A method for testing flip-chip packages comprising:
   aligning a microscope and a test engine;
   placing a flip-chip package between the microscope and the test engine;
   attaching an acoustic transducer to the flip-chip package;
   delivering an impact from the test engine to the flip-chip package;
   recording in a computer acoustic information from the acoustic transducer attached to the flip-chip package; and,
   recording image information from the microscope about the flip-chip package.

2. The method of claim 1 further comprising:
   selectively adjusting the test engine for a different location on the same flip-chip package.

3. The method of claim 1, where the impact is delivered to the flip-chip package on a side of the flip-chip package opposite to the side of the flip-chip package to which the acoustic transducer is attached.

4. The method of claim 1, where the acoustic transducer is attached to the side of the flip-chip package having solder balls.

5. A method of testing flip-chip packages comprising:
   loading a JEDEC tray with a pre-determined number of packages;
   choosing a sequence of packages and locations on each package for testing;
   aligning a microscope and a test engine;
   attaching an acoustic transducer to a first flip-chip package;
   delivering an impact from the test engine to the flip-chip package;
   recording in a computer acoustic information from the acoustic transducer attached to the flip-chip package;
   recording image information from the microscope about the flip-chip package;
   continuing testing the flip-chip package at a different location in the sequence until a pre-determined number of locations on the package have been tested; and,
   continuing testing on the next package in the sequence.

6. The method of claim 5, where the impact is delivered to the flip-chip package on a side of the flip-chip package opposite to the side of the flip-chip package to which the acoustic transducer is attached.

7. The method of claim 5, where the acoustic transducer is attached to the side of the flip-chip package having solder balls.

8. A method of testing flip-chip packages comprising:
   choosing a holder for a pre-determined set of packages under test;
   choosing a sequence of packages and locations on each package for testing;
   placing the packages under test in the holder;
   aligning a microscope and a test engine;
   attaching an acoustic transducer to a first flip-chip package;
   delivering an impact from the test engine to the flip-chip package;
   recording in a computer acoustic information from the acoustic transducer attached to the flip-chip package;
   recording image information from the microscope about the flip-chip package;
   continuing testing the flip-chip package at a different location in the sequence until all locations on the package have been tested; and,
   continuing testing on the next package in the sequence.

9. The method of claim 8, where the impact is delivered to the flip-chip package on a side of the flip-chip package opposite to the side of the flip-chip package to which the acoustic transducer is attached.

10. The method of claim 8, where the acoustic transducer is attached to that side of the flip-chip package having solder balls.

* * * * *